United States Patent
Quinn et al.

[11] Patent Number: 5,876,354
[45] Date of Patent: Mar. 2, 1999

[54] BIOPSY NEEDLE HUB ASSEMBLY

[75] Inventors: Brad Quinn, Indianapolis; Dan C. Ireland, Martinsville; Michael E. Miller, Indianapolis, all of Ind.

[73] Assignee: EMX, Indianapolis, Ind.

[21] Appl. No.: 639,528

[22] Filed: May 1, 1996

[51] Int. Cl.⁶ .................................................. A61B 10/00
[52] U.S. Cl. ...................... 600/562; 600/564; 600/567; 606/167; 606/170
[58] Field of Search .................................. 128/749, 751, 128/752, 753, 754; 606/167, 172, 184, 185, 170; 600/562, 564, 567, 563

[56] References Cited

U.S. PATENT DOCUMENTS

| | | | |
|---|---|---|---|
| 4,699,154 | 10/1987 | Lindgren | 128/754 |
| 5,121,751 | 6/1992 | Ranalletta | 128/754 |
| 5,163,947 | 11/1992 | Kvlo et al. | 606/151 |
| 5,195,533 | 3/1993 | Chin et al. | 128/754 |
| 5,306,260 | 4/1994 | Kanner | 128/754 |
| 5,388,589 | 2/1995 | Davis | 128/749 |
| 5,392,790 | 2/1995 | Kanner et al. | 128/753 |
| 5,476,101 | 12/1995 | Schramm et al. | 128/754 |
| 5,546,957 | 8/1996 | Heske | 128/749 |

*Primary Examiner*—Richard J. Apley
*Assistant Examiner*—Justine R. Yu
*Attorney, Agent, or Firm*—Beck, Michael & Beck, P.C.

[57] ABSTRACT

An automatic tissue sampling device includes a housing having an upper opening and a cover closable over the opening. A biopsy needle assembly is operatively disposed within the device, and includes an outer cannula and an inner stylet. A drive mechanism includes a cannula carriage and a stylet carriage slidably disposed within the housing and a system of springs for driving the first and second carriages to pierce a tissue site and obtain a tissue sample. The cannula and stylet of the needle assembly are each supported on the respective carriages by corresponding hubs. The hubs are configured to be received within the carriages to impart driving motion from the carriages to the needle assembly. In one aspect of the invention, the hubs each include a flag attached to the hub and projecting laterally away from the longitudinal axis of the hub. Each flag is sized to be manually grasped to install or remove the hubs from the carriages. The hubs also include a tab projecting outward from the hub opposite the flag. The tabs can be configured to reside within tab slots defined in each of the carriages to lock the hubs to the carriages in axial motion.

12 Claims, 10 Drawing Sheets

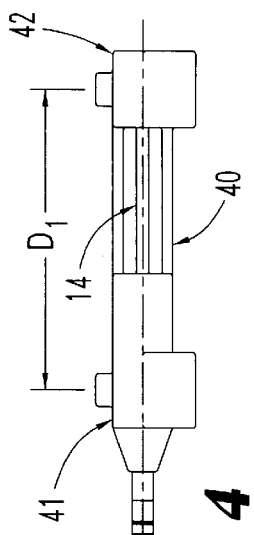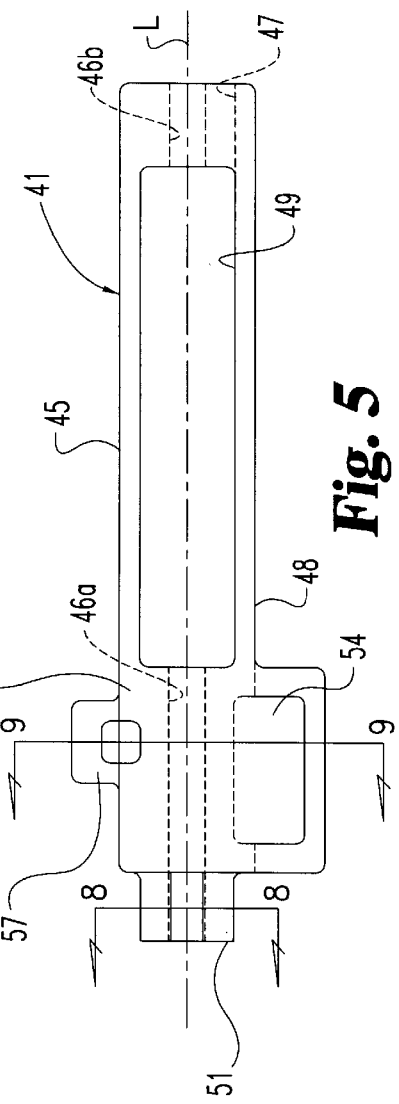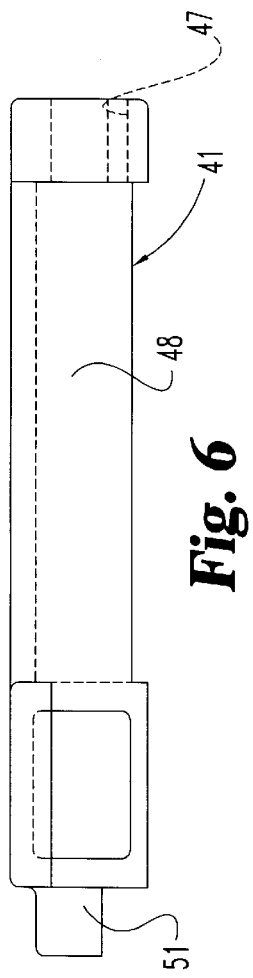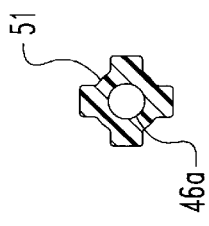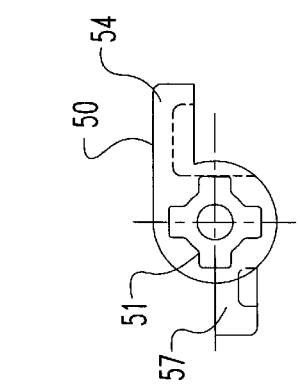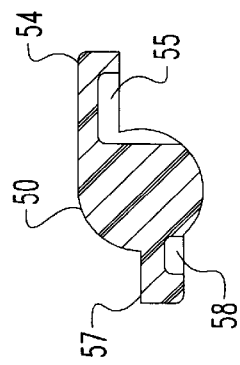
Fig. 4
Fig. 5
Fig. 6
Fig. 7
Fig. 8
Fig. 9

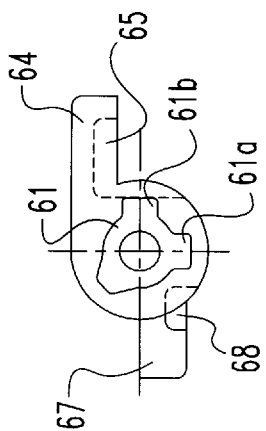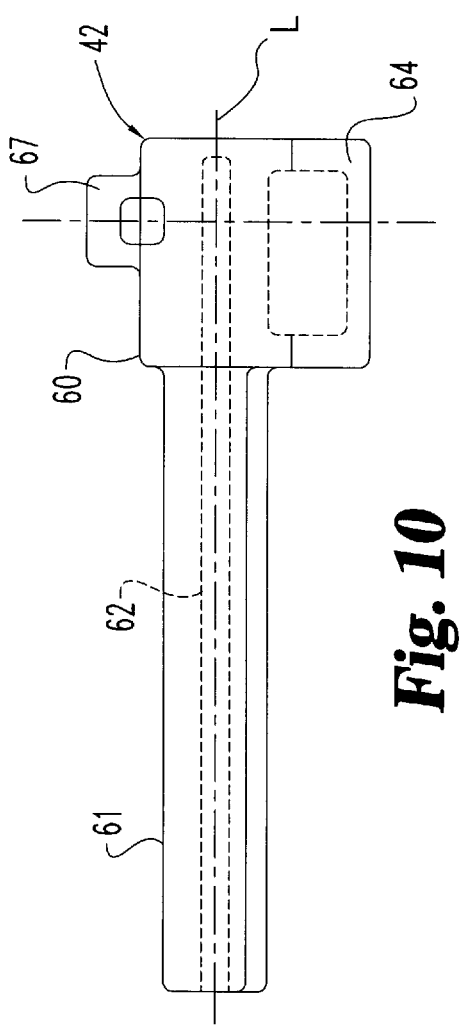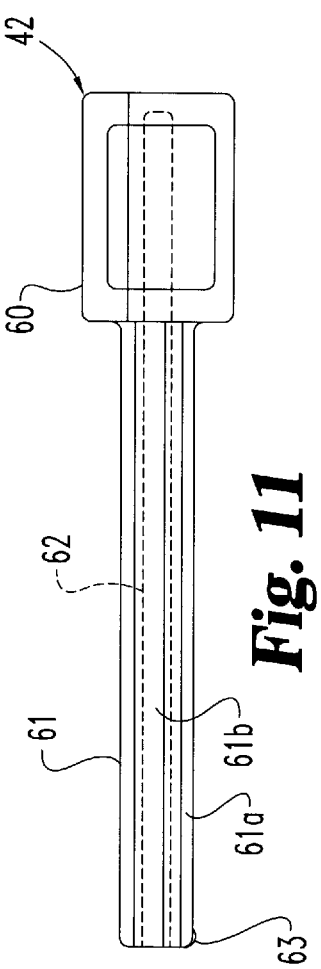

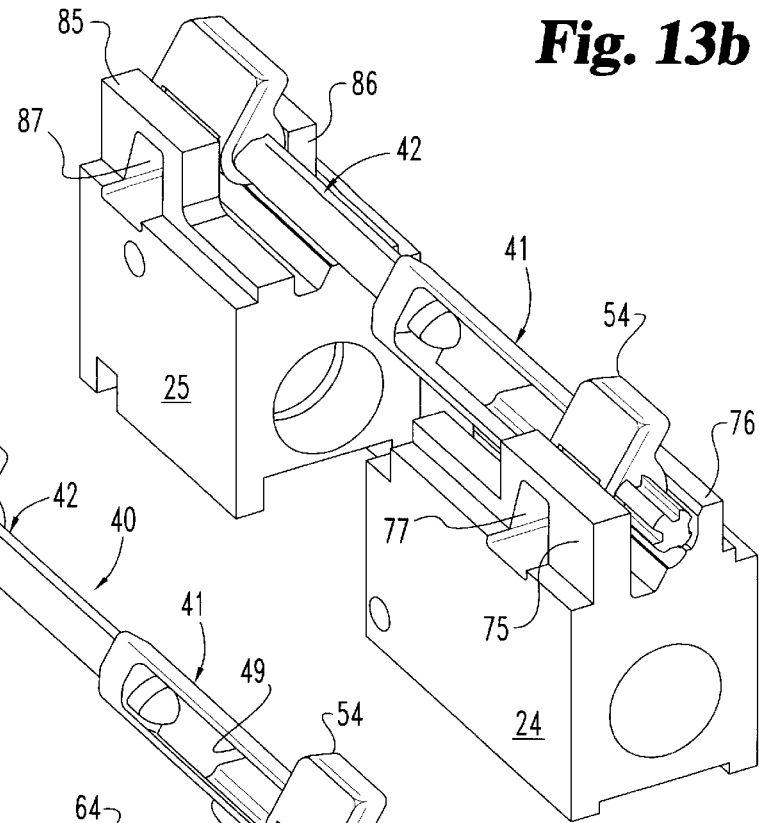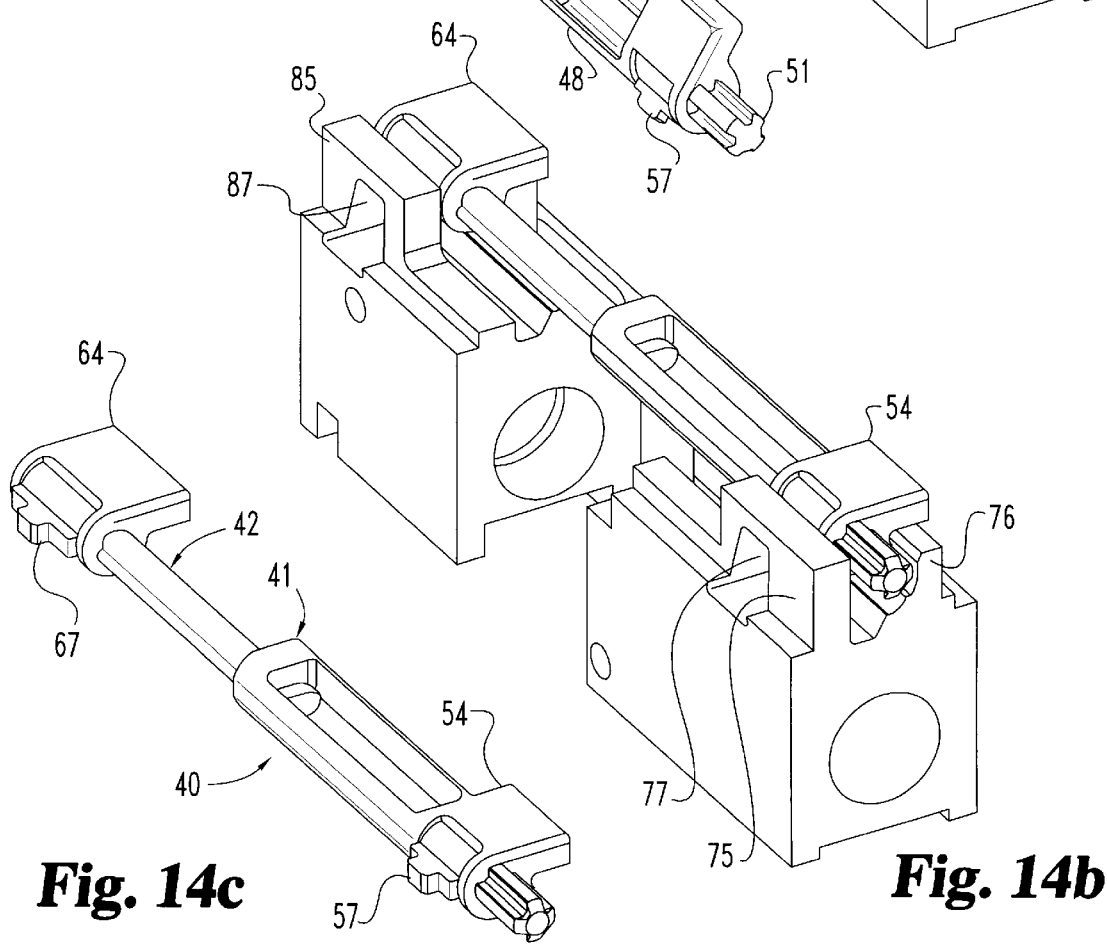

BIOPSY NEEDLE HUB ASSEMBLY

BACKGROUND OF THE INVENTION

The present invention relates to tissue sampling or biopsy devices, and in particular to an automatic tissue sampling apparatus for utilizing two piece biopsy needle systems. In a specific aspect, the invention concerns a needle hub assembly for use with the automatic tissue sampling apparatus.

A typical biopsy needle system may be utilized in obtaining tissue samples from a patient which includes two coaxial needles. The first needle generally consists of a substantially solid shaft in the form of a stylet having a cutting point at its end to facilitate insertion of the needle into the tissue to be sampled. The second needle is typically hollow in the form of a cannula and is disposed about the first inner needle.

In manual biopsy needle systems, the two needle components each have handles at their ends for manual operation. To obtain the tissue sample, the biopsy needle is inserted into the patient into the specific target tissue, preferably at the center of a desired cell mass to be investigated. The two needles are then reciprocated relative to each other to trap tissue within the outer needle cannula. Typically, the outer needle is held stable while projecting the first inner needle or stylet forward a short distance to penetrate the tissue. Then with the outer needle held stable, the inner stylet is retracted, severing the adjacent tissue and confining the tissue within the outer cannula. The entire biopsy needle assembly can then be withdrawn and the tissue sample sent for pathological examination.

In order to facilitate the tissue sampling operation, automatic tissue sampling or biopsy apparatus have been developed. One such device is depicted in U.S. Reissue Pat. No. 34,056 to Lindgren et al. This patent shows a tissue sampling device in which the two needles of the biopsy needle system are driven by a series of compressed springs. Each of the needles is supported by a hub, which hub is removably mounted within a respective slide or carriage. The actuating springs operate on the carriages to drive the stylet into the target tissue and then the outer cannula over the stylet to extract the tissue sample.

Another automatic tissue sampling device is shown in U.S. Pat. No. 5,284,156 to Shramm et al. This patent shows a biopsy apparatus that utilizes a different driving and actuation mechanism from that shown in the prior Lindgren patent. However, as with most automatic biopsy devices, the sampling apparatus in the Shramm patent also utilizes a carriage assembly to support hubs within which each of the needles are engaged.

The details of automatic tissue sampling or biopsy apparatus of this type can be easily gleaned from either the Lindgren or the Shramm patents. In accordance with the present invention, a tissue sampling apparatus 10, such as shown in FIGS. 1, 2, is provided which is similar in operation to the device shown in the Shramm U.S. Pat. No. 5,284,156. This biopsy device 10 includes a drive unit 11 which supports a biopsy needle assembly 12. As described above, the biopsy needle assembly 12 includes an outer cannula 13 and a concentrically disposed stylet 14. The stylet defines a tissue recess 15 which is used to capture and excise target tissue. The drive unit 11 includes a drive unit housing 17 that is provided with a hinged cover 18 to permit access to the internal workings of the drive unit 11. Many of the internal components of the drive unit are shown in FIG. 2. It is understood that the representation of tissue sampling device 10 in FIGS. 1, 2 is simply for purposes of illustration and that the device includes other components that are not depicted in the figures for clarity.

The particular tissue sampling device 10 shown in these figures can be a device sold as the MBD (Multiple Biopsy Device)™ manufactured and marketed by Engineered Medical Systems, Inc., of Indianapolis, Ind. The details of the structure and operation of the MBD™ can be easily discerned from the product itself. However, for purposes of illustration in connection with the present invention, a general description of the components of the sampling device 10 will follow. In particular, the drive unit housing 17 is closed not only by the hinged cover 18 but also by a front end plate 19 and an opposite end plate 21. The front end plate 19 includes a slot 20 defined therein through which a biopsy needle assembly 12 extends. A support frame 22 is mounted within the drive unit housing 17 and includes a carriage stop 23 which restricts the longitudinal motion of the carriages within the unit.

The cannula and stylet of the biopsy needle assembly 12 are supported within the sampling device 10 by a cannula carriage 24 at the forward end of the device and a rear stylet carriage 25. The drive mechanism of the device includes a series of springs. A return spring 27 operates to provide a resistive force against reciprocation of the cannula carriage 24. A nest spring 28 and pusher spring 29 provide the actuation force to drive the two carriages 24, 25 forward into the tissue site. A center tube 30 extends through the cannula carriage 24 to maintain the coaxial alignment of the carriages and to support the shaft portion of the actuator handle 32. The actuator handle operates to cock the carriages 24, 25 into their operative positions. A latch 31 engages the carriages to hold them in their loaded or energized positions until the latch is released.

As thus illustrated, the tissue sampling device 10 is similar to automatic devices currently available in the marketplace. With these devices, the biopsy needle assembly 12 can be removed and sterilized and re-inserted into the same drive unit. Alternatively, a pre-sterilized disposable biopsy needle can be provided that fits into the carriages 24, 25 of the device. However, one difficulty with this approach is that the needle hubs affixed to the coaxial needles are often small and difficult to manipulate. In addition, the physician may have to spend time manipulating the hubs to properly position them within the carriages of whatever automatic biopsy device is being used. Finally, another difficulty encountered with these devices utilizing replaceable biopsy needle assemblies is that the assemblies are not easy to remove once a tissue sample has been obtained. Simple and safe removal is essential to protect the physician and to protect the excise tissue sample.

There is a need in the industry for a hub for use with a removable and replaceable biopsy needle assembly that is ergonomically efficient and is economical to produce. In addition, the hub should permit easy placement within the biopsy sampling device, and particularly in the carriages of the device.

SUMMARY OF THE INVENTION

These need in the field of automatic biospy devices are met by the novel biopsy needle hub and hub assembly of the present invention. The hub is configured for use in mounting a tubular member, such as a biopsy needle or cannula, within a carriage of a tissue sampling device. In the preferred embodiment, the tissue sampling device has a housing within which the carriage is slidably disposed for longitudinal motion within the housing. A carriage is provided for both the outer cannula and the inner stylet, each carriage including a recess or channel within which a respective hub of the novel hub assembly is disposed.

In one aspect of the invention, each hub of the hub assembly includes a body defining a longitudinal axis and configured to be received within the recess of the carriage for rotation about the longitudinal axis. Each body further defines a bore along the longitudinal axis for receiving one of the tubular members therein. Each hub body also includes a flag attached to said body and having a length parallel to the longitudinal axis and a width transverse to the length, with the width of said flag extending outward from said body. The flag is configured to be manually grasped by the physician or technician to insert or remove the hub assembly from the recesses in the tissue sampling device carriages.

In one aspect of the invention, the tissue sampling device has a cover closable over the housing for containing the needle and hub assemblies within the housing. The width of the flag is sized so that when each hub body is received within the recess or channel of the carriage and the flag is positioned projecting away from the recess, the cover cannot be closed over the housing.

In a further aspect, each carriage of the tissue sampling device has a slot transverse to the recess. Each of the hubs can then further comprises a tab attached to the body and extending away from the flag. The tab is sized to be received within the slot when the hub body is received within the channel.

Another feature of the inventive hub assembly includes an interconnection mechanism for interconnecting the cannula hub and the stylet hub. In one embodiment, this interconnection mechanism includes an elongated shaft attached to the body of one hub, such as the stylet hub. The cannula hub further includes a sleeve within which the shaft is slidably received, thereby permitting relative axial movement between the two hubs. Preferably, the shaft and sleeve are configured to prohibit relative rotation between the two hubs.

It is one object of the present invention to provide a hub assembly for use with a needle assembly that can be removably disposed within an automatic tissue sampling device. A further object of the novel hub assembly is realized by features that provide a visual indication that the hubs are or are riot properly oriented within the tissue sampling device, and that physically prevents operation of the device until the hubs are properly oriented.

Another object of the invention resides in providing a hub assembly that provides a positive lock between the hub assembly supporting the cannula and stylet, and the carriage and drive mechanism of the automatic tissue sampling device. Other objects and specific benefits of the present invention can be discerned from the following written description and accompanying figures.

BRIEF DESCRIPTION OF THE DRAWINGS

FIG. 4 is a side elevational view of the biopsy needle assembly depicted in FIG. 3, shown with the inventive hub assembly.

FIG. 5 is a top elevational view of the cannula hub portion of the hub assembly shown in FIG. 4.

FIG. 6 is a side elevational view of the cannula hub shown in FIG. 5.

FIG. 7 is an end elevational view of the cannula hub shown in FIGS. 5 and 6.

FIG. 8 is a cross-sectional view of the cannula hub taken at line 8—8 in FIG. 5 as viewed in the direction of the arrows.

FIG. 9 is a cross-sectional view of the cannula hub taken along line 9—9 in FIG. 5 as viewed in the direction of the arrows.

FIG. 10 is a top elevational view of the stylet hub component of the hub assembly depicted in FIG. 4.

FIG. 11 is a side elevational view of the stylet hub shown in FIG. 10.

FIG. 12 is an end elevational view of the stylet hub shown in FIGS. 10 and 11.

FIG. 13b is a left side perspective view of the hub assembly and the carriages shown in FIG. 13a.

FIG. 13c is a left side perspective view of the hub assembly disposed within the carriages shown in FIGS. 13a and 13b.

FIG. 14b is a left perspective view of the hub assembly and carriages as shown in FIG. 14a.

FIG. 14c is a left perspective view of the hub assembly that is engaged within the carriages shown in FIGS. 14a and 14b.

DESCRIPTION OF THE PREFERRED EMBODIMENTS

Figure 1:
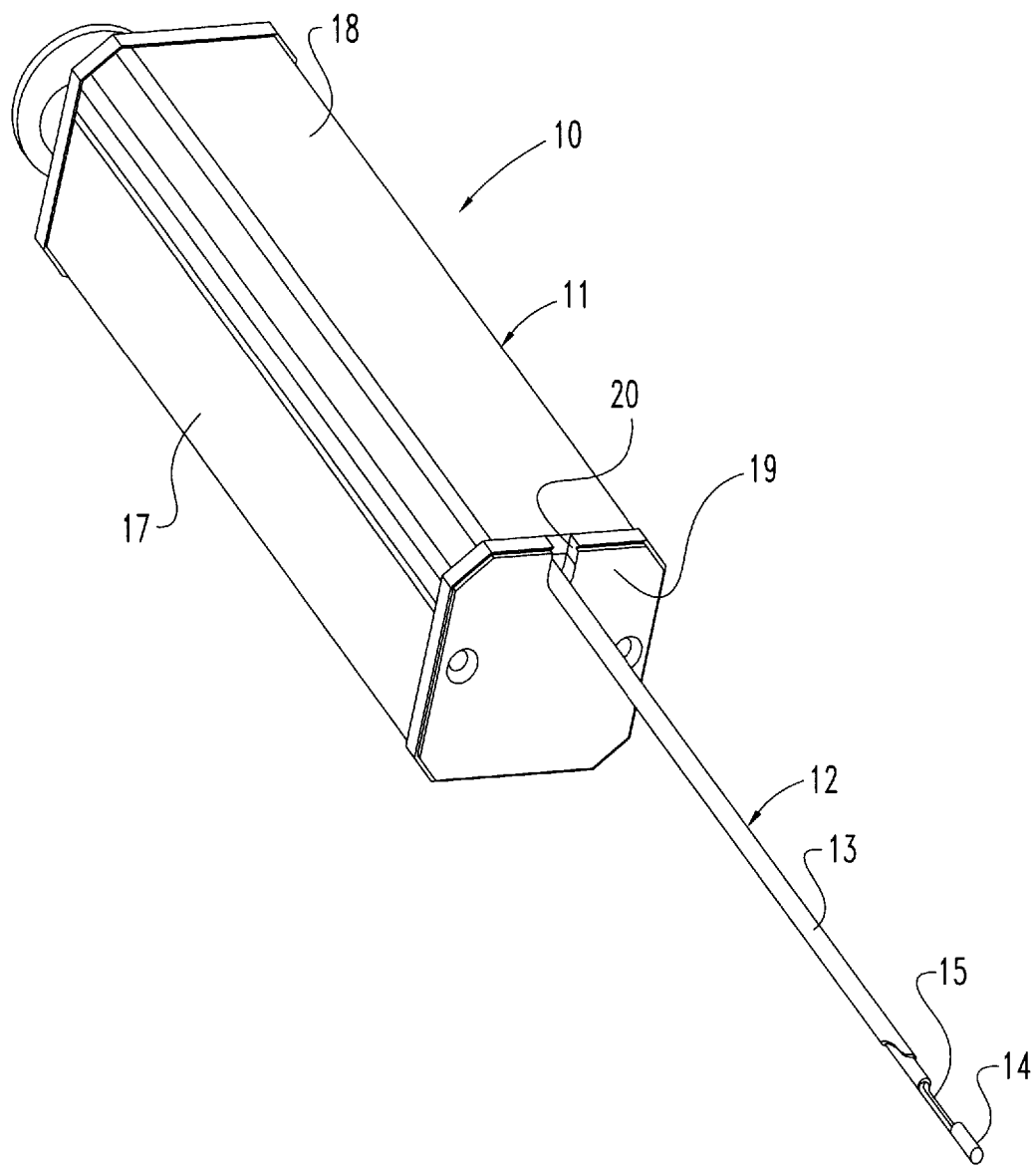
FIG. 1 is a top perspective view of a tissue sampling device of known design.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention contemplates a hub assembly for use with a removable biopsy needle assembly. The removable biopsy needle assembly is configured to be supported by sliding carriages within an automatic tissue biopsy device. The hub assembly is ergonomically efficient for the physician to place the biopsy needle assembly within the tissue sampling device. The hub assembly also provides an automatic safety mechanism to prevent closing the cover of the device until the hubs are properly and securely mounted within the carriages. The hub assembly of the present invention also provides an ergonomically simple manner for removal of the biopsy needle assembly from the tissue sampling device.

Figure 2:
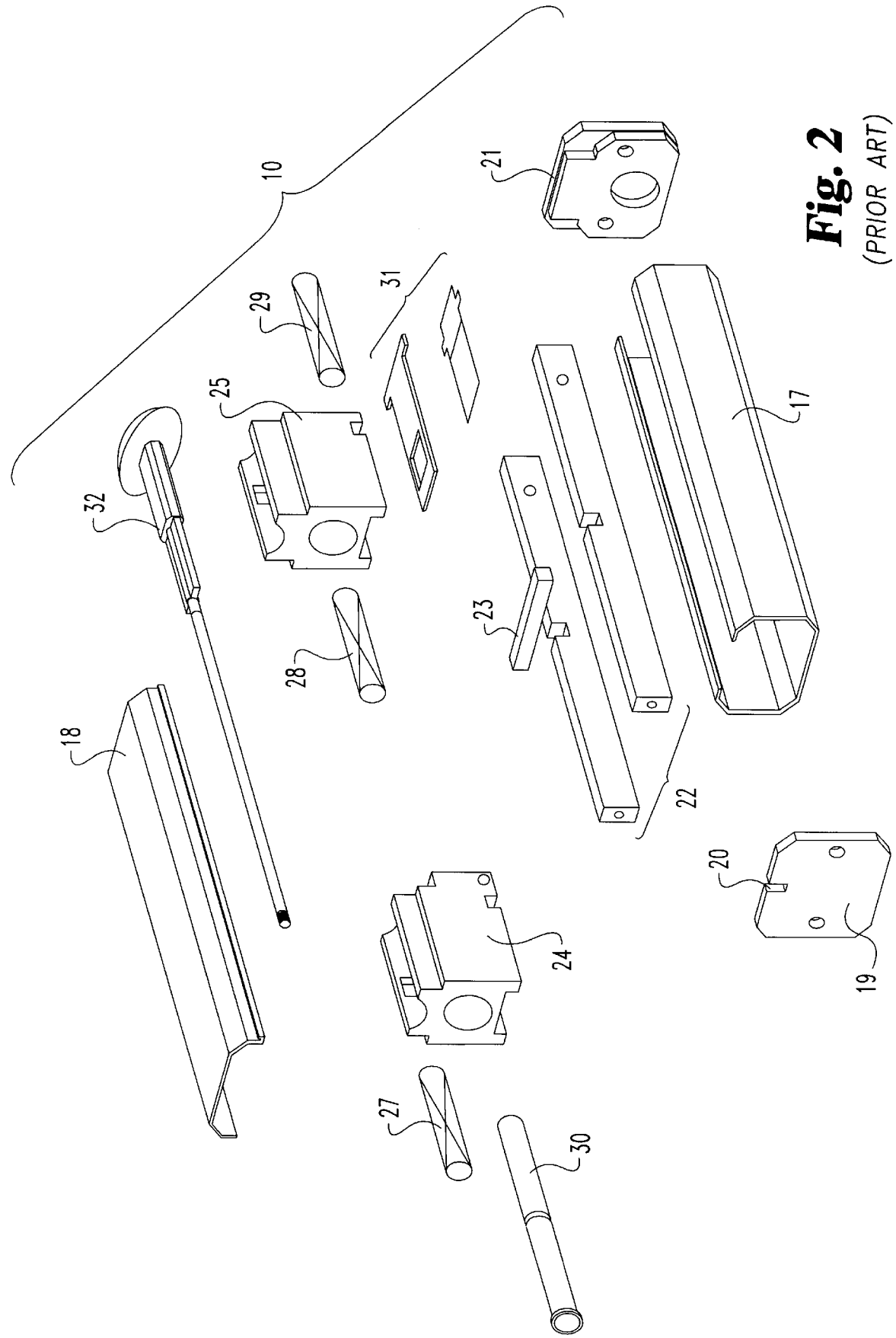
FIG. 2 is an exploded view of the tissue sampling device shown in FIG. 1.
Figure 3:
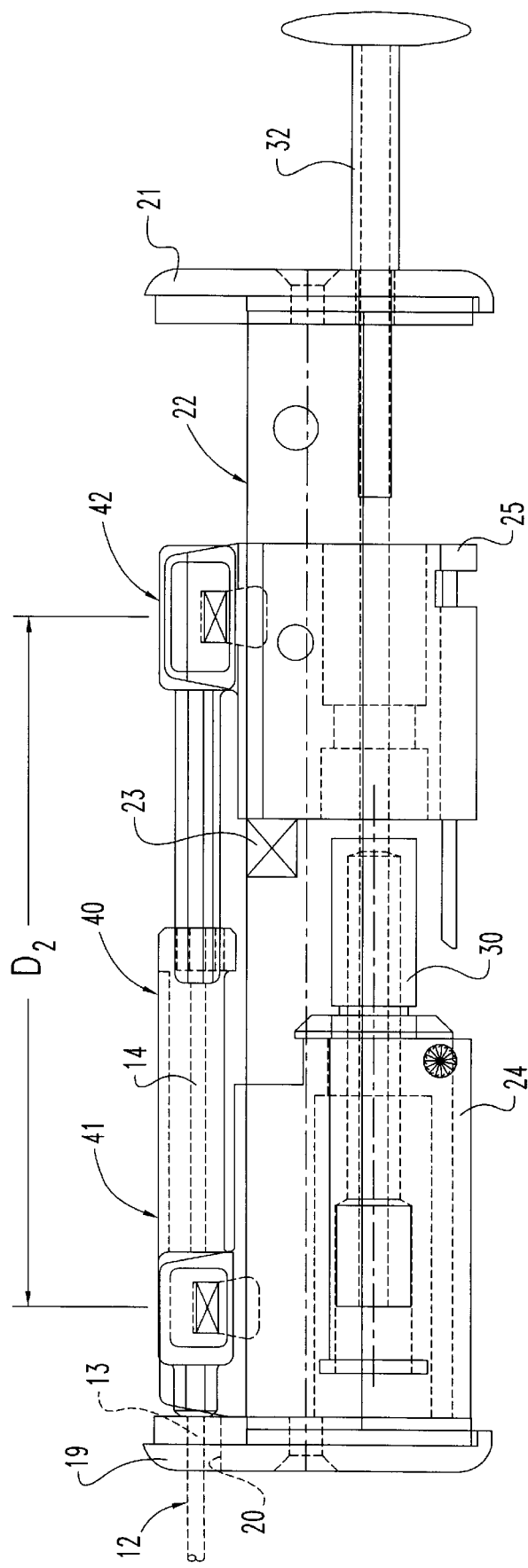
FIG. 3 is a partial cut-away view of a tissue sampling device as shown in FIGS. 1, 2, with a biopsy needle assembly engaged within the carriages of the device.

In accordance with one embodiment of the invention, a hub assembly 40 (FIG. 3) is configured for engagement within a tissue sampling device 10, such as shown in FIGS. 1, 2. As depicted in FIG. 3, the hub assembly 40 includes a cannula hub 41 which is supported by the cannula carriage 24, and a stylet hub 42 which is supported by the stylet carriage 25. The hubs 41 and 42 are slidable relative to each other so that as the carriages are driven by the several springs in the drive unit 11, the hubs, and therefore their respective cannula 13 or stylet 14 (FIG. 1), can axially reciprocate relative to each other to penetrate the tissue site and excise the target tissue.

The details of the cannula hub 41 are depicted in FIGS. 5–9. The cannula hub 41 includes a hub body 45 defining coaxial bores 46a and 46b at opposite ends of the body. At least the bore 46a is configured to receive the cannula 13 therein. Preferably, the bore 46a is formed in and through a cannula support body portion 50 and a stem 51. The cannula 13 can be epoxied or fixed in some conventional manner within the body portion 50 and stem 51 so that is securely affixed to the cannula hub 41.

The bore 46a and the opposite end of the cannula hub 41 is sized to receive the stylet 14 there through. In addition, the bore 46b defines alignment grooves 47 in an L-shaped pattern (not shown). The significance of the alignment grooves 47 will be explained in connection with the description of the stylet hub 42.

The cannula hub 41 includes a sleeve 48 spanning between the opposite ends of the hub. The sleeve 48 defines a slot 49 from top to bottom through the hub body 45. The sleeve 48 in essence provides length to the cannula hub 41 to help in the positioning of the hub assembly and the orientation of the cannula hub 41 relative to the stylet hub 42. Since the sleeve 48 does not carry any load during operation of the tissue sampling device, the sleeve need not be solid. Consequently, the slot 49 is formed in the sleeve 48 to minimize the amount of material necessary in forming the sleeve 48 and the cannula hub 41.

In an important aspect of the present invention, the cannula support body portion 50 defines a flag 54 projecting laterally from the longitudinal axis L of the cannula hub 41. Preferably, the flag projects tangentially from the cylindrical surface of the support body portion 50. On the opposite side of the body portion 50 from the flag 54 is a tab 57. Like the flag, the tab 57 projects generally perpendicular from the longitudinal axis L. The flag 54 is sized and configured to permit easy manual grasping of the flag to manipulate the cannula hub 41. Preferably, the flag 54 can define a relief recess 55 (FIG. 9) on its underside surface to help minimize the amount of material that is necessary to fabricate the cannula hub 41. Likewise, the tab 57 can include a relief recess 58, again to reduce the amount of material required for the device.

As shown in FIGS. 7 and 9, the cannula hub body 45 is generally cylindrical in configuration so that the cannula hub 41 can be pivoted about the body 45, and more specifically about the body portion 50. The stem 51 through which the cannula 13 extends can be in the form of a cross, as shown in FIG. 8. This configuration allows the use of minimum material to form the stem while also retaining adequate strength to support the biopsy cannula 13.

The stylet hub 42 is shown in FIGS. 10–12. In particular, the stylet hub 42 includes a hub body 60 which includes a shaft 61 extending therefrom. A bore 62 is defined through the shaft 61 and body 60 along the longitudinal axis L. When the cannula hub 41 and stylet hub 42 are engaged to form the hub assembly 40, the longitudinal axes L are colinear between each of the hubs 41, 42.

The shaft 61 is generally cylindrical in configuration with a pair of right angle alignment keys 61a and 61b defined thereon. The alignment key 61a, 61b are shown more clearly in FIG. 12. These keys fit within similarly configured alignment grooves 47 in the cannula hub body 45 of the cannula hub 41. In forming the hub assembly 40, the shaft 61 of the stylet hub 42 extends through the bore 36a of the cannula hub body 45 with the alignment keys 61a, b disposed in corresponding ones of the alignment grooves 47. In this manner, the alignment key prevents rotation of the stylet hub 42 relative to the cannula hub 41 and also provides a specific fixed orientation of the two hubs relative to each other. The shaft 61 of the stylet hub 42 is slidable within the sleeve 48 and bore 46b of the cannula hub 41. The two hubs 41 and 42 are slidable relative to each other so that the hubs can be moved from a relative distance $D_1$ between the tabs 57, 67 of the two hubs, as shown in FIG. 4, to a longer length $D_2$, as shown in FIG. 3.

Like the cannula hub 41, the stylet hub 42, and particularly the stylet hub body 60 defines a flag 64 projecting generally perpendicularly from the axis L. The flag 64 can also define a relief recess 65 on its underside surface. In addition, the stylet hub 42 includes a tab 67 formed on the opposite side of the body 60 from the flag 64, which can also bear a relief recess 68.

In a further aspect of the preferred embodiment, the shaft 61 includes a dimple 63 defined at its free end. Preferably, the dimple 63 is formed in one of its alignment keys 61a. This dimple helps keep the stylet hub 42 from disengaging from the cannula hub 41 when the shaft 61 is extended through the bore 46b and sleeve 48 of the cannula hub 41. Most preferably, the dimple 63 is oriented on the shaft 61 so that the hub dimple will hold the two hubs 41, 42 at the distance $D_2$ shown in FIG. 3. At this distance $D_2$ the hubs 41, 42 of the hub assembly 40 are properly oriented for placement within the tissue sampling device 10 when the two carriages 24 and 25 are their unloaded or non-energized positions. When the carriages 24 and 25 are pulled back to their energized positions by way of the actuator handle 32 the cannula hubs 41 and 42 of the hub assembly 40 are at a distance $D_1$ as shown if FIG. 4. At this distance, the dimple 63 is not needed to hold the hubs, 41, 42 together.

The use of the hub assembly 40, and particularly the benefits obtained by the flags 54, 64 and tabs 57 come 67 are depicted in FIGS. 13a–13d and 14a–14d. The FIGS. 13a–13d show the hub assembly 40 as it is inserted within the carriages 24, 25, while the FIGS. 14a–14d show the hub assembly in its position to permit closing of the cover 18 onto the drive unit housing 17.

Figure 13A:
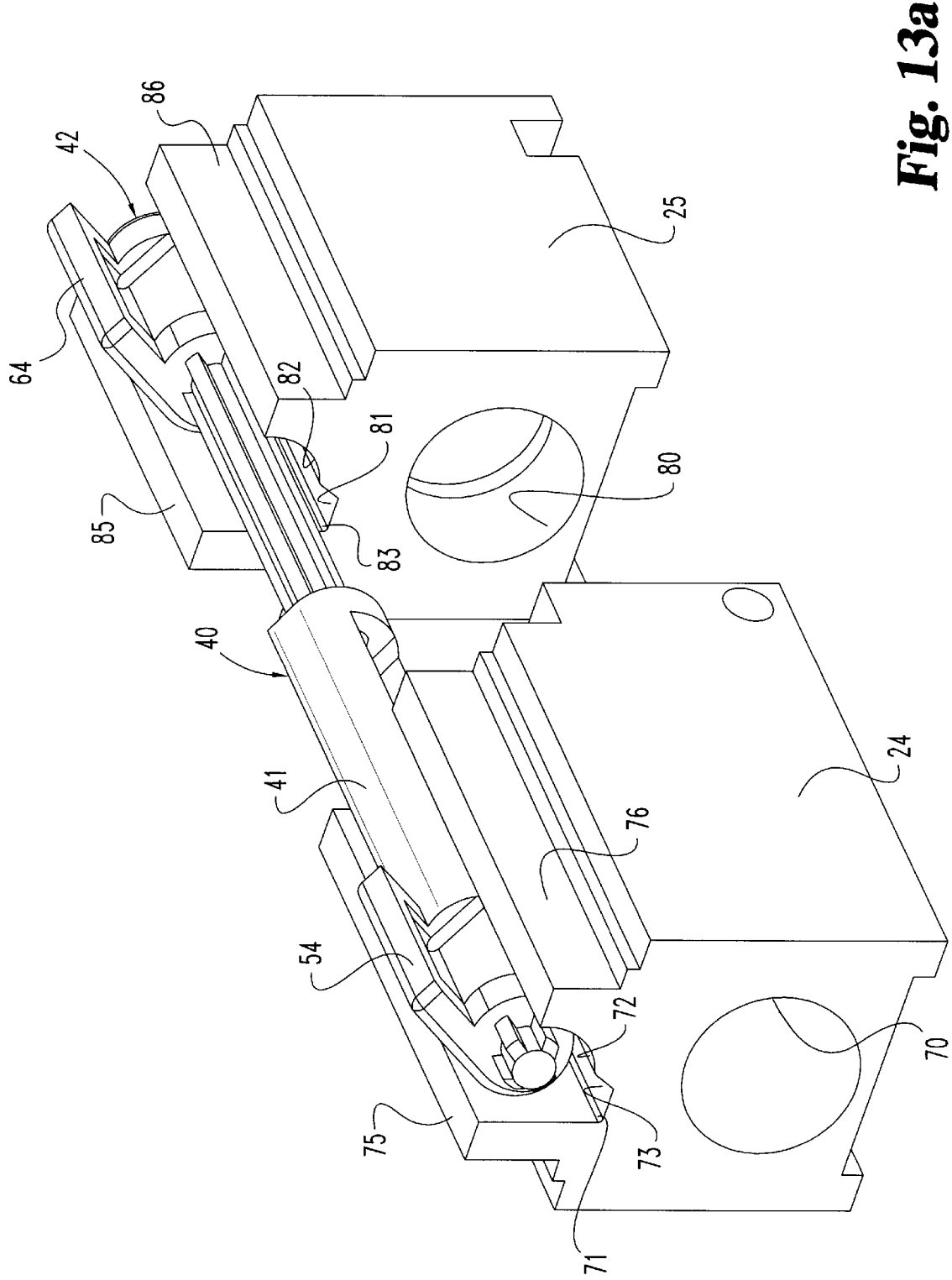
FIG. 13a is a right side perspective view of the hub assembly of FIG. 4 mounted within the carriages of a tissue sampling device.

Referring first to FIGS. 13a and 13b, further details of the carriages 24 and 25 can be seem. In particular, the cannula carriage 24 includes a drive spring bore 70 through which the handle and drive spring mechanism extend. Likewise, the stylet carriage 25 includes a coaxially aligned drive spring bore 80. Each carriage includes a hub channel 71, 81 defined along its length. The hub channels 71, 81 include a cylindrical portion 72, 82 and a tab channel 73, 83. The hub channels 71, 81 are configured to receive the cannula hub body 45 and stylet hub body 60, respectively, hence the cylindrical configuration.

Figure 13D:
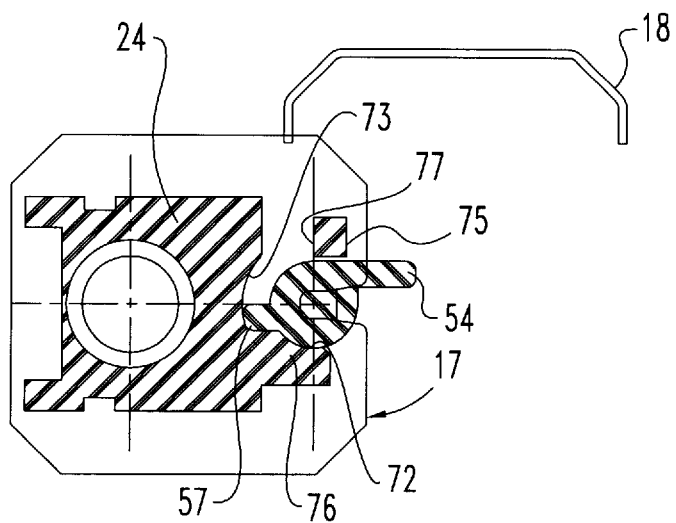
FIG. 13d is an end cross-sectional view of the cannula hub of the hub assembly engaged within the hub carriage as disposed within the drive unit housing.

Each of the carriages 24, 25 includes a tab flange 75, 85, and a flag flange 76, 86 on opposite sides of the hub channels 71, 81. The flanges 75, 76 and 85, 86 help define the respective hub channels 71, 81. As shown in FIG. 13d, the tab flanges 75, 85 define a tab slot 77, 87 which opens into or intects each of the tab channels 73, 83.

When the hub assembly 40 is mounted within the tissue sampling device 10, the physician or technician can then extend the cannula hub 41 and stylet hub 42 to their longest engaged length $D_2$ (FIG. 3) so that the dimple 63 is engaged within the groove 46b of the cannula hub body 45. The physician then can grab either of the flags 54 or 64 to hold the hub assembly 40 and drop it into the tab slots 77, 87 of the two carriages 24, 25. In this position, as shown in FIG. 13c, the tabs 57, 67 will fit into the tab channels 73, 83 with the flags 54, 64 extending upward, as shown in FIG. 13d. In this position, the cover 18 cannot be closed over the drive unit housing 17 because the flags are projecting above the surface of the drive unit housing 17. The flags 54, 64 also provide a visual indication that the device 10 is not yet ready for use.

Figure 14D:
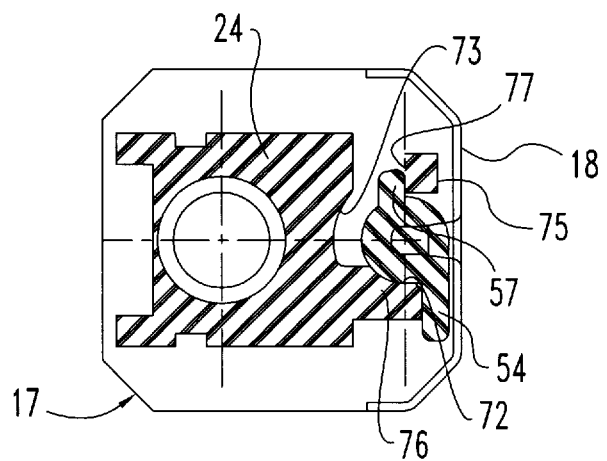
FIG. 14d is an end cross-sectional view of the cannula hub and carriage with the hub shown in its closed configuration within the drive unit housing and cover.
Figure 14A:
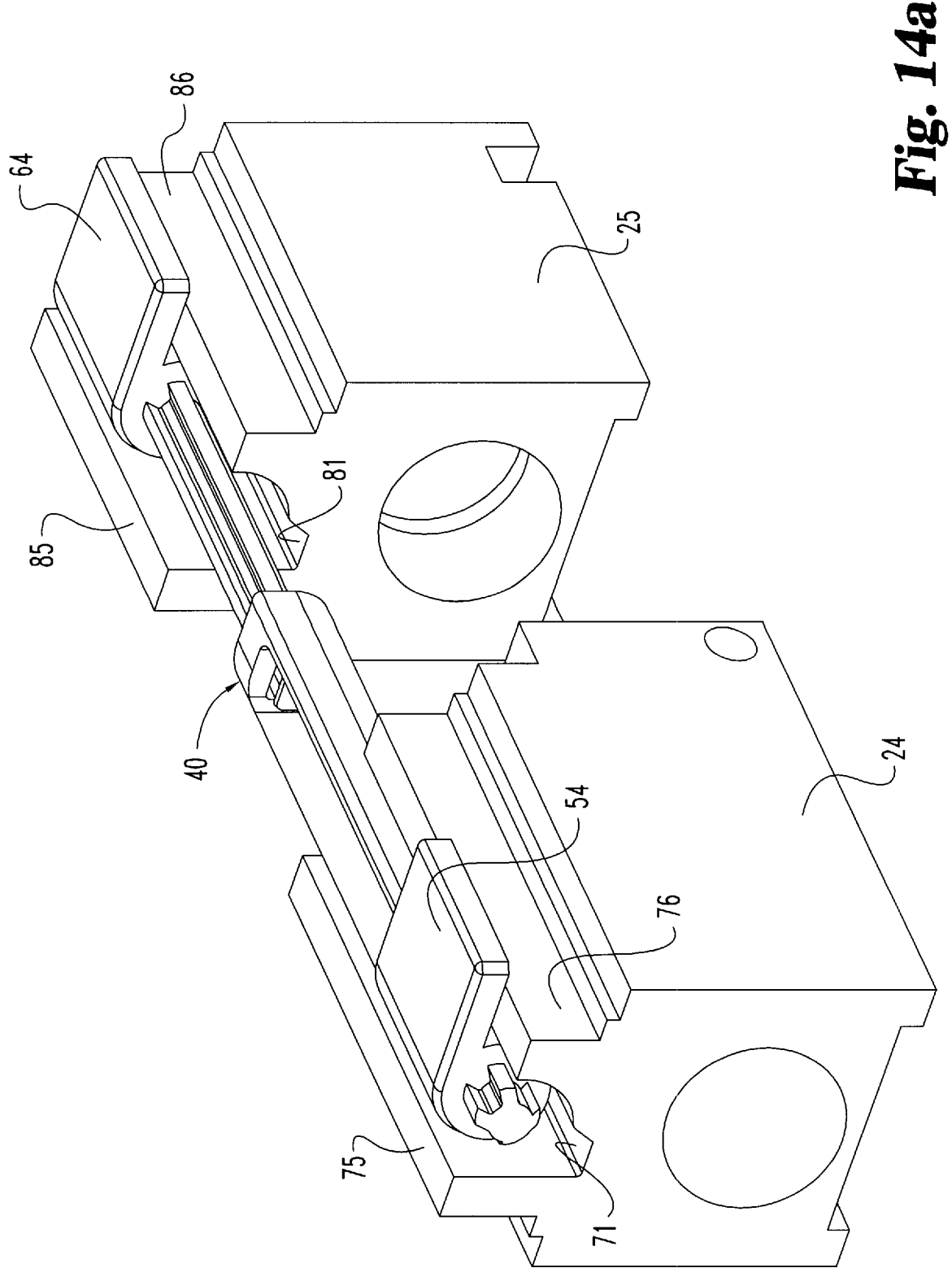
FIG. 14a is a right side perspective view of the hub assembly of FIG. 4 shown in its closed position within the carriages.

At this point, the physician can simply press one of the flags 54, 64 down until the flags contact the respective flags flanges 76, 86, as shown in FIGS. 14a–14d. In this orientation, the hub assembly 40 is still at its extended length, but the flags 54, 64 and tabs 57, 67 are now generally horizontal, as shown in FIG. 14c. As shown more clearly in FIG. 14d, the tabs 57, 67 sweep through the respective tab channels 73, 83 and into the tab slots 77, 87 defined in the tab flanges 75, 85. In this orientation, the flags 54, 64 are essentially flush with the drive unit housing 17 so that the cover 18 can now be closed. Simultaneously, the tabs 57, 67 are locked within the tabs slots 77, 87 to fix the position of the hub assembly 40 relative to the carriages 24, 25. In other words, when the tabs 57, 67 are disposed within the respective tab slots 77, 87, the hubs 41, 42 cannot slide axially relative to the carraiges 24, 25. A projection (not shown) may also be defined on the flag flanges 75, 76 to extend into the relief recesses 65, 75 of each of the flags, in order to provide additional fixation of the hub assembly 40 to the carriages 24, 25.

In the preferred embodiment, the flags 54, 64 are sized for easy grasping by the surgeon. Preferably, the flags 54, 64 are rectangular in configuration with a width of about 0.3–0.4 inches from the longitudinal axis L (see FIG. 5) and a length of about 0.5 inches. It has been found that these dimensions are sufficient to be grasped between the thumb and index finger. The addition of the relief recesses 65, 75 on the underside of the flags 64, 74 can also provide additional gripping surface for the surgeon or technician. The tabs 57, 67 are preferably about 0.26 inches long from the longitudinal axis L with a width of about 0.2 inches. The tab slots 77, 87 in the tab flanges 75, 85 are sized so that the tabs 57, 67 will snuggly fit within the slots. Preferably, these tab slots 77, 87 have a width of about 0.21 inches for a tight tolerance about the hub assembly tabs.

The remaining dimensions of the cannula hub 41 and stylet hub 42 can be determined by the particular tissue sampling device in which they are to be engaged. In one specific embodiment the cannula hub has an overall length of 2.1 inches with the hub body 45 being generally cylindrical at a diamond or of about 0.32 inches. In this specific embodiment, the sleeve 48 has a length of about 1.23 inches with a thickness of 0.05 inches on either side of the slot 49. Again in this specific embodiment, the shaft 61 of the stylet hub 42 has a length of about 1.425 inches so that it can extend fully into the length of the sleeve 48 through the bore 46b of the cannula hub body 45. It is understood that these length dimensions can be modified to fit other tissue sampling devices.

Preferably the components to the hub assembly 40 are formed of a plastic material. In one specific embodiment, the material is Idamitsu IR220 poly-carbonate.

Figure 15:
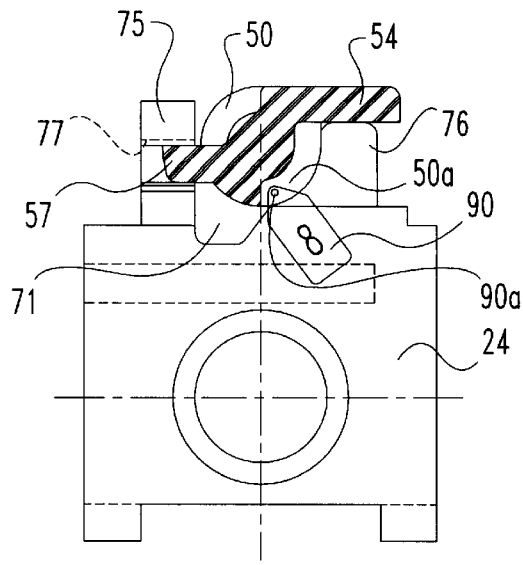
FIG. 15 is an end partial cross-section view of one embodiment of a retention device used to retain the position of the hub assembly within the carriages.

In a further aspect of the invention, a retention device can be provided to hold the hub assembly 40 in its closed position as shown in FIGS. 14a–14d. In one specific embodiment, the retention device comprises a ball detent 90 that is supported within each of the carriages 24, 25, as shown in FIG. 15. In accordance with this embodiment, the cannula hub body portion 50 can include a recess 51a which receives the ball 90A of the ball detent 90. As with a typical ball detent, the ball detent 90 of the present embodiment is slidable and retractable as the body portion 50 is pivotable with the tab channel 71. In the open position, that is with the flag 54 projecting upward as shown in FIGS. 13a, 13d, the ball detent is pushed aside by the cylindrical part of the body portion 50. As the cannula hub assembly 40 is rotated into its closed position the ball detent slips into the recess 50a preferably providing both a tactile and an audible confirmation that the hub assembly 40 is now in its proper closed position. In addition, the ball detent 90 will provide some resistance to disengagement of the hub assembly 40 from the two carriages 24, 25 even as the tissue sampling device 10 is moved about prior to closing the cover 18.

Figure 16:
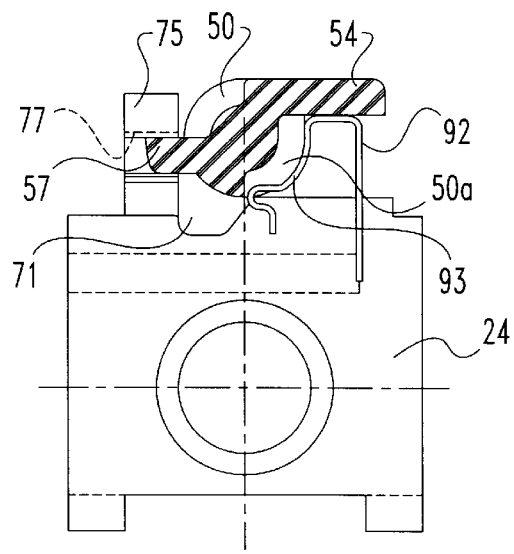
FIG. 16 is an end partial cross-section view of an alternative embodiment of the retention device for retaining the position of the hub assembly within the carriage in its closed position.

In a further specific embodiment, the retention device includes a flat spring 92 as depicted in FIG. 16. The flat spring 92 is again support within each of the carriages 24, 25. In this embodiment, the flat spring 92 defines a cam portion 93 that contacts the cannula body portion 50 of the cannula hub 41. This cam portion moves aside when the hub assembly is first placed within the tab channel 71. The cam portion 93 then deflects downward as the cannula hub body 45 is rotated until the cam portion 93 reaches the recess 50a, at which time it clicks into place to hold the hub assembly in position.

Figure 17:
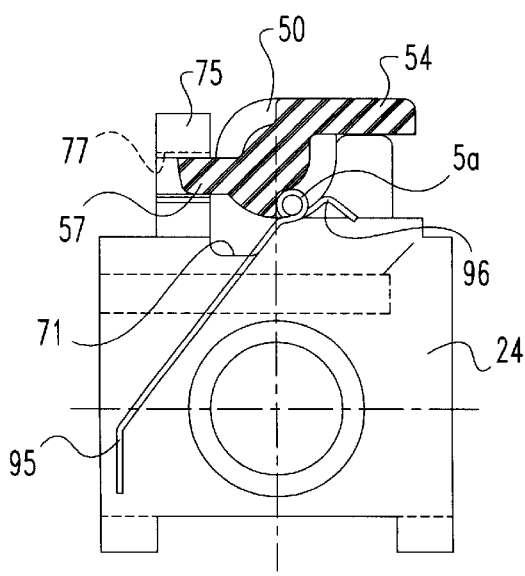
FIG. 17 is an end partial cross-section view of a further embodiment of a retention device for maintaining the hub assembly in its closed position within the carriages.

In yet a further specific embodiment, a retention device 95 is shown in FIG. 17. In this embodiment, the retention device is a wire spring 95 (as opposed to the flat plate spring 92). Again, the wire spring 95 is mounted within each of the carriages 24, 25. The wire spring 95 is preferably bent into a cam portion 96 adjacent the tab slots 71, 81. The operation of this wire spring embodiment 95 of the retention device is similar to the other retention devices.

The present invention contemplates a hub assembly for use in a wide variety of automatic tissue sampling devices. The hub assembly in accordance with one aspect of the present invention provides a flag which give a visual of the position of the hub assembly within the carriages of the sampling device. In addition, the flag prevents closure of the cover over the device if the hubs are not properly situated and locked within their respective carriages. The invention further contemplates elements to hold the hub assemblies within the carriages so that they cannot be readily disengaged during operation of the tissue sampling device. Finally, the flags provided by the invention give the surgeon an easy means to both insert and remove the hub assemblies from the tissue sampling device.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A biopsy needle hub for use in mounting a tubular member within a carriage of a tissue sampling device, in which the tissue sampling device has a housing within which the carriage is slidably disposed for longitudinal motion within the housing, the tissue sampling device also including a cover closable over the housing for containing the tubular member within the housing, and further in which the carriage includes a longitudinal channel for receiving the biopsy needle hub therein, said hub comprising:

a substantially cylindrical body defining a longitudinal axis and rotatable about said axis within the channel of the carriage, said body further defining a bore along said longitudinal axis for receiving the tubular member therein;

a flag extending substantially tangentially from said body and having a length parallel to said longitudinal axis of said body and a width transverse to said length, said width of said flag extending outwardly from said body; and said hub rotatable within said channel between a first position and a second position, wherein in said first position said flag is positioned projecting away from the channel, said width of said flag sized to prevent the cover from being closed over the housing when the hub is in the first position, and in said second position said flag is positioned within the channel to permit closing of the cover over the housing.

2. The biopsy needle hub assembly according to claim 1, in which the carriage of the tissue sampling device has a slot transverse to the longitudinal channel and a channel communicating between the slot and the longitudinal channel, wherein said hub further comprises a tab attached to said body and extending away from said flag, said tab sized to be received within the tab channel when said body is received within the channel in said first position and said tab engageable into said slot when said body is in said second position.

3. The biopsy needle hub according to claim 2 wherein said tab and said flag extend away from said body 15 in radially opposite direction.

4. The biopsy needle hub according to claim 1, wherein said length and width of said flag define an area sized to be manually grasped to place said hub within or remove said hub from the channel of the carriage.

5. The biopsy needle hub according to claim 1, further comprising:

an elongated shaft attached to said body and extending along said longitudinal axis, said shaft defining a channel therethrough mating with said bore to receive the tubular member therein.

6. A biopsy needle hub assembly for use in mounting a coaxially disposed biopsy needle and cannula within respective first and second carriages slidably disposed for longitudinal motion within the housing of a tissue sampling device, the tissue sampling device also including a cover closable over the housing for containing the needle and cannula within the housing, and further in which each carriage includes a longitudinal, said hub assembly comprising:

a first hub having a first substantially cylindrical body defining a longitudinal axis and rotatable about said axis within the channel of the first carriage of the tissue sampling device, said first body further defining a first bore along said longitudinal axis for receiving the biopsy needle therein;

a second hub having a second substantially cylindrical body further defining the longitudinal axis and rotatable about said axis within the channel of the second carriage, said second body further defining a second bore along said longitudinal axis to receive the cannula therein;

a flag extending substantially tangentially outward from at least one of said first body and said second body and having a length parallel to said longitudinal axis of said body and a width transverse to said length, said width of said flag extending outwardly from said at least one body;

an interconnection mechanism disposed between and interconnecting said first hub and said second hub, said interconnection mechanism permitting relative linear movement between said first and second hubs along said longitudinal axis while preventing relative rotation between said first and second hubs about said longitudinal axis; and said hub assembly rotatable within said channel between a first position and a second position, wherein in said first position said flag is positioned projecting away from the channel, said width of said flag sized to prevent the cover from being closed over the housing when the hub assembly is in the first position and in said second position, said flag is positioned within the channel to permit closing of the cover over the housing.

7. The biopsy needle hub according to claim 6, wherein said width of said flag is sized so that when said at least one body is received within the channel of the respective carriage and said flag is positioned projecting away from the channel, the cover cannot be closed over the housing.

8. The biopsy needle hub assembly according to claim 6, in which each carriage of the tissue sampling device has a slot transverse to the longitudinal channel and a tab channel communicating the slot to the longitudinal channel, wherein each of said first and second hubs further includes a tab attached to said first and second body respectively, said tab sized to be received within the tab channel of the corresponding carriage when the respective body is received within the longitudinal channel in said first position and said corresponding tab engageable into said corresponding slot when each said body is in said second position.

9. The biopsy needle hub assembly according to claim 6, wherein both of said first and second bodies include a flag projecting therefrom.

10. The biopsy needle hub assembly according to claim 6, wherein said interconnection mechanism includes:

an elongated shaft attached to said first body and extending along said longitudinal axis, said shaft defining a first channel therethrough mating with said first bore to receive the biopsy needle; and an elongated sleeve attached to said second body and extending along said longitudinal axis, said sleeve defining a second channel therethrough mating with said second bore and sized to slidably receive said elongated shaft therein.

11. The biopsy needle hub assembly according to claim 10, wherein said interconnection mechanism further includes a key and groove arrangement between said shaft and said sleeve to prevent relative rotation therebetween about said longitudinal axis.

12. The biopsy needle hub assembly according to claim 10, wherein:

said sleeve has a second free end opposite said second body; and said shaft has a first free end opposite said first body, said first free end including a dimple defined thereon for engaging said sleeve when said dimple is at said free end of said sleeve.

* * * * *

UNITED STATES PATENT AND TRADEMARK OFFICE
CERTIFICATE OF CORRECTION

PATENT NO. : 5,876,354
DATED : March 2, 1999
INVENTOR(S) : Brad Quinn et al.

It is certified that error appears in the above-identified patent and that said Letters Patent is hereby corrected as shown below:

Col. 3, line 45
  replace "are riot"
  with --are not--.

Col. 9, line 39
  replace "a channel"
  with --a tab channel--.

Signed and Sealed this

Twentieth Day of July, 1999

Attest:

Q. TODD DICKINSON

*Attesting Officer*  *Acting Commissioner of Patents and Trademarks*